United States Patent [19]
Diaz et al.

[11] Patent Number: 5,871,764
[45] Date of Patent: Feb. 16, 1999

[54] SKIN TONING FORMULATION

[75] Inventors: Teresita Diaz, Perth Amboy; Claudia Kaminski, Milford; Phyllis Mitchell, Morristown, all of N.J.

[73] Assignee: Johnson & Johnson Consumer Products, Inc., Skillman, N.J.

[21] Appl. No.: 609,016

[22] Filed: Feb. 29, 1996

[51] Int. Cl.$^6$ ............................ A61K 7/00; A61K 7/02; A61K 7/48

[52] U.S. Cl. .................. 424/405; 424/401; 424/489; 424/70.1; 424/78.03

[58] Field of Search .................................. 424/401, 70.1, 424/78.03, 489, 405

[56] References Cited

U.S. PATENT DOCUMENTS

| | | | |
|---|---|---|---|
| 4,355,028 | 10/1982 | Klingman et al. | 424/230 |
| 4,883,659 | 11/1989 | Goodman | 424/78 |
| 5,139,782 | 8/1992 | Jung | 424/401 |
| 5,422,112 | 6/1995 | Williams | 424/401 |
| 5,534,265 | 7/1996 | Fowler | 424/489 |
| 5,538,728 | 7/1996 | Yanaki | 424/401 |
| 5,702,709 | 12/1997 | Schulz et al. | 424/401 |

FOREIGN PATENT DOCUMENTS

| | | |
|---|---|---|
| 0 281 812 A1 | 9/1988 | European Pat. Off. . |
| 0 412 449 A3 | 2/1991 | European Pat. Off. . |
| WO 86/05394 | 9/1986 | WIPO . |

*Primary Examiner*—Anthony C. Caputa
*Assistant Examiner*—Mary K Zeman

[57] ABSTRACT

The invention provides for skin cleanser and astringent compositions comprising an oil-absorbing powder, a thickening agent, a keratolytic agent and an alcohol. The compositions also comprise water, fragrances, colorants, an emollient and a humectant.

20 Claims, No Drawings

SKIN TONING FORMULATION

DESCRIPTION OF THE PRIOR ART

End-users are becoming increasingly aware that undesirable skin conditions can be caused or aggravated by inherent skin oil or by oils found in various products including cosmetics. One of the most undesirable skin conditions is acne.

Prior art skin cleansing compositions have attempted to absorb oil and debris from skin surfaces. These skin cleansing compositions can be described variously as oil-based, emulsion-type or water-based surfactant systems.

Oil-based skin cleansing compositions contain a mixture of oils and esters. These compositions can be an irritant particularly when used on sensitive skin, because they may contain surfactants and because they tend to leave a greasy film over the skin. Emulsion-type skin cleansing compositions are usually based on a class of surfactants known as emulsifiers. Any surfactants can be irritant, especially when used around the eyes.

Oil-in-water emulsions are the most common, but water-in-oil emulsions are also available. Emulsion-type preparations contain oil and/or waxes and tend to leave a greasy feel on the skin.

To alleviate this problem, U.S. Pat. No. 5,480,633 attempts to provide for an aqueous skin rinse formulation for soap and surfactant residues. The claim is made that the facial rinse provided by the invention is effective in reducing the deposition of soap and surfactants from the skin.

There exists products which attempt to visibly control oily facial shine via oil-absorbing powders. These products do not possess antiseptic properties, and furthermore, are aesthetically unappealing by virtue of their viscous, chalky appearance, and/or lack of homogeneity.

The present invention provides for non-oily leave-on skin cleansing compositions having astringent, antiseptic, oil-stripping properties with long lasting oil control.

SUMMARY OF THE INVENTION

The present invention provides for leave-on skin cleanser compositions having astringent, antiseptic and oil stripping properties. The compositions comprise as essential ingredients an oil-absorbing powder, thickening and keratolytic agents and alcohol. The compositions of the invention also comprise water, fragrances, colorants, an emollient and a humectant. The oil-absorbing powder is in an amount from about 1 to about 3 wt %, the thickening agent in an amount from about 0.1 to about 1 wt. %, the keratolytic agent in an amount from about 0.01 to about 2 wt. % and the alcohol in an amount from about 10 to about 40 wt. %.

The invention also provides for a method of preparing the compositions of the invention. The oil-adsorbing powder and the thickening agent are admixed in water to form a suspension. The pH of the suspension is adjusted to from about 3 to about 4. The keratolytic agent is dissolved in alcohol to form an acid-alcohol mixture and the pH of the mixture adjusted to from about 3 to about 4. The suspension and the acid-alcohol mixture are combined and the pH adjusted to from about 3 to about 4. A humectant is admixed with the suspension and an emollient is mixed with the acid-alcohol mixture.

The invention further provides for a method for cleansing the skin. The method comprises the step of applying to the skin an effective amount of the compositions of the invention, allowing the applied composition to dry completely and then leaving the dried compositions on the skin area for continual oil absorbancy and shine control.

DESCRIPTION OF THE PREFERRED EMBODIMENTS

The novel compositions of this invention provide for an aqueous topical formulation having astringent, antiseptic and oil stripping properties.

The novel compositions comprise four classes of essential ingredients in a suitable carrier. The four classes are generally defined as oil absorbing powders, thickening agents, keratolytic agents and a lower alkyl alcohol.

The oil absorbing powder is any substance which is capable of removing oil secretions from the skin. Exemplary oil absorbing powders include cornstarch, oatmeal, talc, silica coated mica, titanium dioxide coated mica and hectorite type-clay. The oil absorbing powder is present in an amount from about 1 to about 3 wt. %, preferably in an amount from about 1.8 to about 2.2 wt. %.

The term "hectorite-type clay" as used herein includes both naturally occurring and synthetic hectorite clays such as those available commercially from Southern Clay Products, Inc., under the trade name Laponite XLS and XLG. They are already known in the art and are used in the personal care and cosmetic areas, namely in such products as shampoos, face masks, moisturizing creams and make-ups. Some of the advantages of Laponite include improving the application and feel of lotions and creams, stabilizing emulsions, suspensions and solutions, reducing the oily feel of emulsions and acting as an absorbent for grease and oil. Laponite is a preferred oil-absorbing powder because it not only contributes to a better feel of the composition but provides immediate visible perception of absorption of skin oil.

The compositions of this invention also include a thickening agent. Exemplary thickening agents include those made from bentonite, carbomer, carrageenan, ozokerite, dextrin, gelatin and a cellulose resin such as xanthan gum. The thickening agent is present in an amount from about 0.1 to about 1 wt. %, preferably in an amount from about 0.23 to about 0.27 wt. %.

Xanthan gum is available commercially under the trade name Keltrol. Xanthan gum is a high molecular weight polysaccharide which has been used in food and pharmaceutical applications. As provided commercially, xanthan gum particles typically range in size from 75 to 250 microns. Xanthan gum is a preferred thickening agent for maximum suspension activity with minimal viscosity.

Compositions of this invention also include a keratolytic agent. Exemplary agents are salicylic acid, boric acid and methyl salicylate. The keratolytic agent is present in an amount from about 0.01 to about 2 wt. %, preferably from about 0.5 to about 1.5 wt. %.

Salicylic acid is known as a topical keratolytic agent and externally as an antiseptic and antifungal agent. Salicylic acid acts as an astringent and accelerates the removal of horny cells by decreasing their stickiness or cohesion. Salicylic acid is a preferred keratolytic agent as it combines maximum efficacy with antisepsis while offering ease of solubilization.

Alcohol is an essential ingredient on the novel compositions of the invention, particularly lower alkyl alcohols. Exemplary alcohols are ethyl alcohol, isopropyl alcohol and mixtures thereof. The alcohol is suitable as a vehicle for the keratolytic agent and acts as an antiseptic and astringent.

The alcohol is present in the compositions in an amount from about 10 to about 40 wt. %, preferably from about 20 to about 30 wt. %.

In addition to the essential ingredients, the compositions of this invention can also contain nonessential ingredients. These are generally humectants, emollients, colorants, fragrances and the like.

Emollients which can be included in the compositions of the invention function by their ability to remain on the skin surface or in the stratum corneum to act as lubricants, to reduce flaking, and to improve the skin appearance. Typical emollients include fatty esters, fatty alcohols, mineral oil, polyether siloxane copolymers and the like. Examples of emollients include but are not limited to PPG-15 stearyl ether, PPG-10 cetyl ether, steareth-10, oleth-8 and PPG-4 lauryl ether. The emollient is preferably PPG-15 stearyl ether and can be present in an amount up to about 5 wt %, preferably up to about 2.5 wt. %.

Humectants of the polyhydric alcohol-type can be included in the compositions of the invention. The humectants aid in increasing the effectiveness of the emollient, reduce scaling, stimulate removal of built-up scale and improve skin feel. Typical polyhydric alcohols include glycerol (also known as glycerin), polyalkylene glycols, and more preferably alkelene polyols and their derivatives, including propylene glycol, dipropylene glycol, polypropylene glycol, polyethylene glycol and derivatives thereof, sorbitol, hydroxypropyl sorbitol, hexylene glycol, 1,3-dibutylene glycol, 1,2,6,-hexanetriol, ethoxylated glycerol, propoxylated glycerol and mixtures thereof. For best results, the humectant is preferably 1,3-dibutylene glycol and can be present in an amount up to about 5 wt. %, preferably up to about 2.5 wt. %.

Additional nonessential components include well known colorants such as FD&C Blue #1 and D&C Yellow #10 and fragrances such as eucalyptus oil, camphor synthetic, peppermint oil and clove oil. For best results, colorants may be present as needed, in an amount up to about 1 wt. %, preferably up to about 0.5 wt. %. Fragrances may be present as needed in an amount up to about 0.5 wt. %, preferably up to about 0.36 wt. %.

According to the present invention, the oil absorbing powder, thickening agent and keratolytic agent are admixed with a suitable vehicle or carrier system. Preferred carriers include water for the oil-absorbing powder and the thickening agent. The water is admixed in an amount as needed and the keratolytic agent is admixed with the alcohol. The nonessential components are admixed where needed in a suitable vehicle or carrier system. Preferred carriers include water for the humectant and alcohol for the emollient and fragrances.

The oil-absorbing powder and thickening agent are first admixed in water to form a suspension. Optionally, a humectant can also be admixed. Following admixing, the pH is adjusted to from about 3 to about 4 using art-known acids. A preferred acid is citric acid.

The keratolytic agent is admixed in alcohol to form an acid-alcohol mixture. Optionally, the emollient and fragrances can also be admixed with the acid-alcohol mixture. Following admixing, the pH is adjusted to from about 3 to about 4 using art-known bases. A preferred base is potassium hydroxide.

The water suspension and the acid-alcohol mixture are combined. Optionally, colorants can be admixed and the pH adjusted to from about 3 to about 4, preferably to from about 3.3 to about 3.5.

The novel compositions of the invention result in a skin cleansing astringent, antiseptic and oil-stripping formulation. The formulation is in the form of an aqueous suspension which can be applied as a leave-on skin cleanser. The compositions of the invention are applied to the face (or other skin surface) and the applied composition is allowed to dry completely. The dried composition is left on the skin surface for continual oil absorbancy and shine control.

The invention will now be further described with reference to the following example:

| PHASE | COMPONENT | wt. % |
| --- | --- | --- |
| A | Water | q.s. to 100 |
|   | Laponite | 2 |
|   | xanthan gum | 0.25 |
|   | 1,3-dibutylene glydol | 2 |
| B | alcohol | 20 |
|   | salicylic acid | 2 |
|   | PPG-15 Stearyl Ether | 2 |
|   | Fragrances | q.s. |
| A + B | Colorants | q.s. |

The abbreviation "q.s." is a standard dispensing nomenclature which means "as needed" or "as sufficient".

Phase A

Laponite is dispersed in the water at room temperature and mixed for a sufficient time until dispersed. Xanthan gum is then added to the dispersion also at room temperature and mixed therein for a sufficient time until the dispersion thickens. Alternatively, xanthan gum can be first dispersed and then the Laponite added. Optionally, 1,3-dibutylene glycol can be added during dispersion formation. The pH of the dispersion is adjusted with an acid to a pH of from about 3 to about 4.

Phase B

The salicylic acid and the alcohol are mixed at room temperature until the acid dissolves in the alcohol. Optionally, PPG-15 stearyl ether and the fragrances can be added. The pH is adjusted with a base to from about 3 to about 4.

Phase A+B

Phases A and B are mixed and optionally, colorants can be added. The pH can be adjusted by addition of an acid or a base where appropriate to a pH of from about 3.3 to about 4. The target pH at the time of manufacture is about 3.5.

While this specification describes the principles of the present invention, it is to be understood that other aspects, advantages and modifications within the scope of the invention will be apparent to those skilled in the art.

We claim:

1. A leave-on skin cleanser and astringent composition comprising an oil-absorbing powder in an amount from about 1 to about 3 weight percent;

a thickening agent in an amount from about 0.1 to about 1 weight percent;

a keratolytic agent in an amount from about 0.01 to about 2 weight percent;

an alcohol in an amount from about 10 to about 40 weight percent, said alcohol selected from the group consisting of ethyl alcohol and isopropyl alcohol; and a pH-adjusting agent which adjusts the pH of the composition to form about 3 to about 4 wherein said composition is in the form of a suspension.

2. The composition of claim 1 further comprising an emollient in an amount from about 0 to about 0.5 weight percent.

3. The composition of claim 1 further comprising a humectant in an amount from about 0 to about 0.5 weight percent.

4. The composition of claim 2 further comprising a humectant in an amount from about 0 to about 0.5 weight percent.

5. A leave-on skin cleanser and astringent composition comprising:

a hectorite-type clay in an amount from about 1 to about 3 weight percent;

xanthan gum in an amount from about 0.1 to about 1 weight percent;

salicylic acid in an amount from about 0.1 to about 2 weight percent;

an alcohol in an amount from about 10 to about 40 weight percent, said alcohol selected from the group consisting of ethyl alcohol and isopropyl alcohol;

wherein said composition has a pH of from about 3 to about 4 and said composition is in the form of a suspension.

6. The composition of claim 5 further comprising PPG-15 stearyl ether in an amount of from about 0 to about 0.5 weight percent.

7. The composition of claim 5 further comprising 1,3-dibutylene glycol in an amount of from about 0 to about 0.5 weight percent.

8. The composition of claim 6 further comprising 1,3-dibutylene glycol in an amount of from about 0 to about 0.5 weight percent.

9. A leave-on skin cleanser and astringent composition comprising:

about 2 weight percent laponite;

about 0.25 weight percent xanthan gum;

about 2 weight percent salicylic acid;

about 20 weight percent alcohol;

wherein said composition has a pH of from about 3 to about 4 and said composition is in the form of a suspension.

10. The composition of claim 9 further comprising about 0.5 weight percent PPG-15 stearyl ether.

11. The composition of claim 9 further comprising about 2 weight percent 1,3-dibutylene glycol.

12. The composition of claim 10 further comprising about 2 weight percent 1,3-dibutylene glycol.

13. A leave-on skin cleanser and astringent composition prepared by the steps of:

admixing in water an oil-absorbing powder in an amount from about 1 to about 3 weight percent and a thickening agent in an amount from about 0.1 to about 1 weight percent to from a suspension, and adjusting the pH of said suspension to from about 3 to about 4;

dissolving a keratolytic agent in an amount from about 0.01 to about 2 weight percent in from about 10 to about 40 weight percent alcohol to form an acid-alcohol mixture, said alcohol selected from the group consisting of ethyl alcohol and isopropyl alcohol, and adjusting the pH of said mixture to from about 3 to about 4; and combining said suspension and said acid-alcohol mixture to form said composition and adjusting the pH of said composition to from about 3 to about 4.

14. The composition of claim 13 which is prepared by the further step of admixing with said suspension a humectant in an amount from about 0 to about 0.5 weight percent.

15. The composition of claim 13 which is prepared by the further step of mixing with said acid-alcohol mixture an emollient in an amount of from about 0 to about 0.5 weight percent and fragrances of from about 0 to about 0.50 weight percent.

16. A leave-on skin cleanser and astringent composition prepared by the steps of:

admixing in water laponite in an amount from about 1 to about 3 wt % and xanthan gum in an amount from about 0.1 to about 1 wt. % to form a suspension, and adjusting the pH of said suspension to from about 3 to about 4;

dissolving salicylic acid in an amount from about 0.01 to about 2 wt. % in from about 10 to about 40 wt % alcohol to form an acid-alcohol mixture, said alcohol selected from the group consisting of ethyl alcohol and isopropyl alcohol, and adjusting the pH of said mixture to from about 3 to about 4; and combining said suspension and said acid-alcohol mixture to form said composition and adjusting the pH of said composition for from about 3 to about 4.

17. The composition of claim 16 which is prepared by the further step of admixing with said suspension 1,3-dibutylene glycol in an amount up to about 0.5 wt. %.

18. The composition of claim 16 which is prepared by the further step of mixing with said acid-alcohol mixture PPG-15 stearyl ether in an amount up to about 0.5 wt. % and fragrances up to about 0.50 wt. %.

19. A method for cleansing the skin comprising the step of applying to the skin an effective amount of the composition of claim 1, allowing the applied composition to dry completely and then leaving the dried composition on the skin area for continual oil absorbancy and shine control.

20. A method of providing continual oil absorbency and controlling shine of facial skin comprising the steps of applying to the face a composition, wherein the composition is in the form of a suspension, and said composition comprises:

an oil-absorbing powder in an amount form about 1 to about 3 weight percent;

a thickening agent in an amount from about 0.1 to about 1 weight percent;

a keratolytic agent in an amount from about 0.01 to about 2 weight percent;

an alcohol in an amount from about 10 to about 40 weight percent, said alcohol selected from the group consisting of ethyl alcohol and isopropyl alcohol;

wherein said composition has a pH of from about 3 to about 4, and said composition being substantially free of surfactant;

permitting said composition to dry completely; and leaving said dried composition on the skin for an extended period.

* * * * *